US008715723B2

(12) United States Patent
Kanios et al.

(10) Patent No.: US 8,715,723 B2
(45) Date of Patent: May 6, 2014

(54) COMPOSITIONS AND METHODS FOR DELIVERY OF AMINO-FUNCTIONAL DRUGS

(75) Inventors: David P. Kanios, Miami, FL (US); Juan A. Mantelle, Miami, FL (US)

(73) Assignee: Noven Pharmaceuticals, Inc., Miami, FL (US)

( * ) Notice: Subject to any disclaimer, the term of this patent is extended or adjusted under 35 U.S.C. 154(b) by 1319 days.

(21) Appl. No.: 11/710,610

(22) Filed: Feb. 26, 2007

(65) Prior Publication Data

US 2007/0212410 A1    Sep. 13, 2007

Related U.S. Application Data

(60) Provisional application No. 60/777,257, filed on Feb. 27, 2006.

(51) Int. Cl.
*A61K 9/52* (2006.01)

(52) U.S. Cl.
USPC .............................................. 424/457

(58) Field of Classification Search
None
See application file for complete search history.

(56) References Cited

U.S. PATENT DOCUMENTS

| | | | |
|---|---|---|---|
| 3,797,494 A | 3/1974 | Zaffaroni | |
| 4,031,894 A | 6/1977 | Urquhart et al. | |
| 4,814,168 A | 3/1989 | Sablotsky et al. | |
| 4,994,267 A | 2/1991 | Sablotsky | |
| 5,474,783 A | 12/1995 | Miranda et al. | |
| 5,601,839 A * | 2/1997 | Quan et al. | 424/448 |
| 5,656,286 A | 8/1997 | Miranda et al. | |
| 5,714,162 A | 2/1998 | Muller | |
| 5,958,446 A | 9/1999 | Miranda et al. | |
| 6,024,974 A * | 2/2000 | Li | 424/448 |
| 6,024,976 A | 2/2000 | Miranda et al. | |
| 6,210,705 B1 * | 4/2001 | Mantelle et al. | 424/448 |
| 6,221,383 B1 | 4/2001 | Miranda et al. | |
| 6,235,306 B1 | 5/2001 | Miranda et al. | |
| 6,316,022 B1 | 11/2001 | Mantelle et al. | |
| 6,465,004 B1 | 10/2002 | Rossi-Montero et al. | |
| 6,537,571 B1 | 3/2003 | Muller | |
| 2002/0077437 A1 | 6/2002 | Silverberg et al. | |
| 2003/0170195 A1 | 9/2003 | Houze et al. | |
| 2004/0086552 A1 * | 5/2004 | Klokkers et al. | 424/449 |
| 2006/0171908 A1 * | 8/2006 | Hanatani et al. | 424/61 |

FOREIGN PATENT DOCUMENTS

| | | |
|---|---|---|
| WO | WO 91/14463 | 10/1991 |
| WO | WO 96/33678 A1 | 10/1996 |
| WO | WO 98/53863 A2 | 12/1998 |
| WO | WO 2006/041911 A2 | 4/2006 |

OTHER PUBLICATIONS

Tan et al. Pressure-sensitive adhesives for transdermal drug delivery systems (Pharmaceutical Science & Technology Today, 2, 60-69, 1999).*
Kanios et al., "Effect of Non-Functional/Non-Reactive Pressure Sensitive Adhesives in Transdermal Drug Delivery Systems," pp. 1-9, 2002.
Nguyen, "In-Vitro to In-Vitro Evaluation for Scopolamine Transdermal Delivery," pp. 1-2, 2002.
Nguyen, V. et al., "In-Vitro to In-Vivo Evaluation for Scopolamine Transdermal Delivery," (Poster presentation at the AAPS meeting in Toronto), 1 page, Nov. 11, 2002.
Kanios, David P. et al., Effect of Non-Functional / Non-Reactive Pressure Sensitive Adhesives in Transdermal Drug Delivery Systems, 9 pgs., Published on May 25, 2003, (Presented at the Pressure Sensitive Tape Council Proceedings, Tech XXVI.

* cited by examiner

*Primary Examiner* — David J Blanchard
*Assistant Examiner* — Tigabu Kassa
(74) *Attorney, Agent, or Firm* — Foley & Lardner LLP

(57) ABSTRACT

Described are flexible, finite systems for the transdermal administration of scopolamine, comprising: (a) a polymer matrix comprising a polymer blend comprising (i) a non-functional acrylic-based polymer constituting at least about 60% by weight of the dry weight of the polymer matrix, and (ii) an amine-resistant capped silicone polymer constituting not more than about 30% by weight of the dry weight of the polymer matrix; and (b) scopolamine solubilized in the polymer matrix, wherein the flexible, finite system is substantially free of vinyl acetate and polar components. In some embodiments, the polymer matrix also comprises a non-polar penetration enhancer. Methods of making and using such flexible, finite systems also are described.

24 Claims, 1 Drawing Sheet

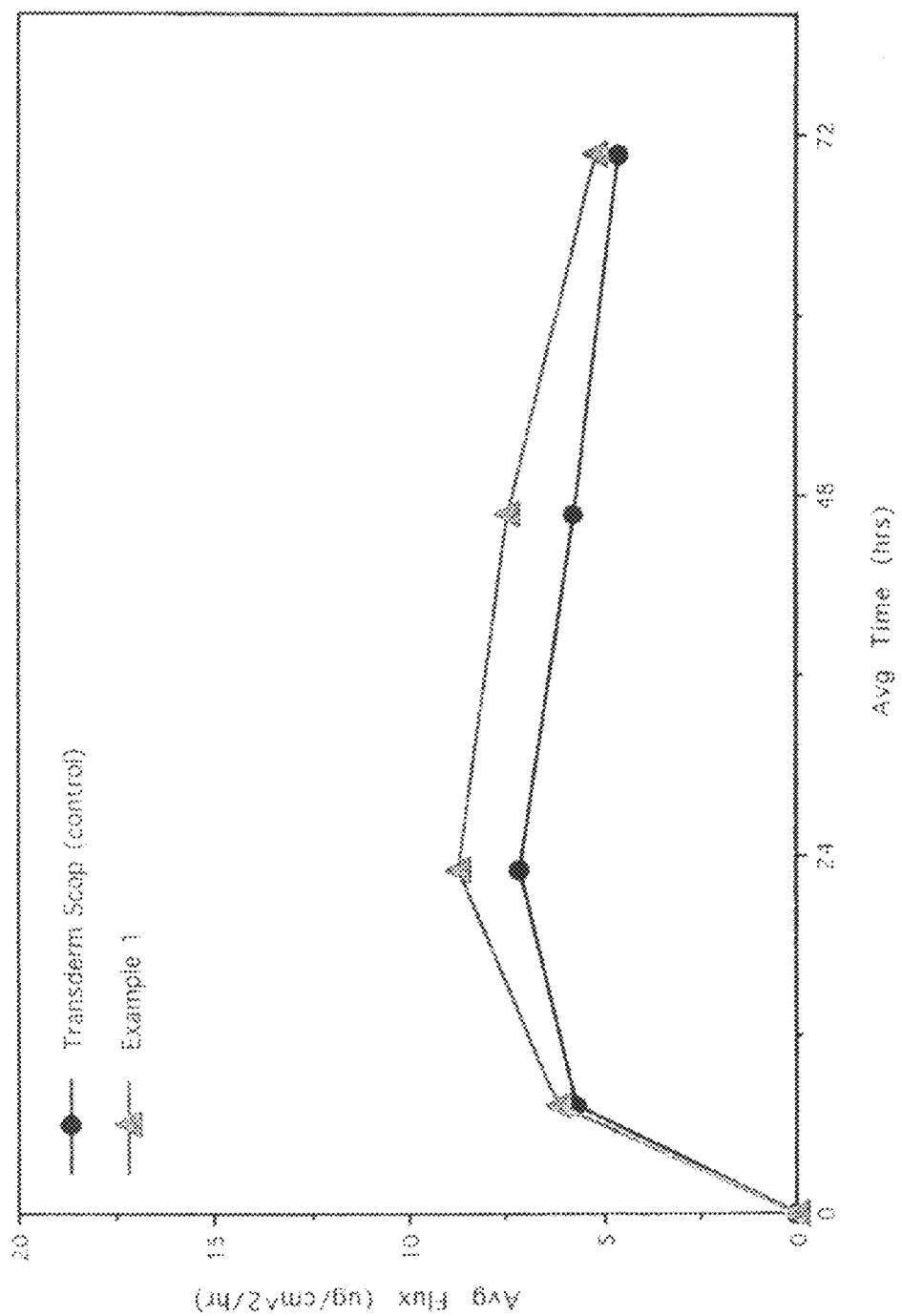

COMPOSITIONS AND METHODS FOR DELIVERY OF AMINO-FUNCTIONAL DRUGS

RELATED APPLICATION

This application claims the benefit of priority from U.S. Provisional Application No. 60/777,257, filed Feb. 27, 2006, the contents of which are incorporated herein by reference.

BACKGROUND OF THE INVENTION

1. Field of the Invention

This invention relates broadly to dermal compositions for the administration of certain drugs, more specifically to amino-functional drugs, and in particular the administration of scopolamine base, from an alternative and improved polymeric matrix without the need for a membrane to control flux of the active substance.

2. Background

Scopolamine is an antiemetic popularly used to avoid nausea and vomiting as for instance occurring while traveling. The antiemetic and antinauseant properties of scopolamine and related compounds have been investigated by administering these compounds orally and intramuscularly. See, e.g., C. D. Wood and A. Graybiel, "Theory of Antimotion Sickness Drug Mechanisms," *Aerosp. Med.* 43: 249-52, 1972; and C. D. Wood and A. Graybiel, "A Theory of Motion Sickness Based on Pharmacological Reactions," *Clin. Pharm.* 11: 621-9, 1970; J. J. Brand and P. Whittingham, "Intramuscular Hyoscine in Control of Motion Sickness," *Lancet* 2: 232-4, 1970.

Optimum drug release rate is an important factor in the prevention of nausea and vomiting accompanying motion sickness and the elimination of parasympatholytic side effects from the drug such as tachycardia, drowsiness and dry mouth. Transdermal administration of scopolamine facilitates the slow, continuous, and controlled release of the drug within the relatively narrow therapeutic window desirable for plasma levels of scopolamine without having to fear the side effects caused by overdose, such as, for example, dryness of the mouth, nausea and sensitivity to glare.

U.S. Pat. Nos. 3,797,494 and 4,031,894 describe the current commercially available product (Transderm Scop®, Novartis) which comprises scopolamine base dispersed in a gelled mixture of mineral oil and polyisobutylene, and relies upon a microporous membrane to control the dosage rate.

U.S. Pat. No. 5,714,162 describes drawbacks to the marketed scopolamine product, in particular drug instability due to crystallization, and describes transdermal delivery systems using polyacrylate adhesives having functional groups as the base polymer, and including polar inactive ingredients and a membrane to improve drug solubility and control flux.

U.S. Pat. No. 6,537,571 describes transdermal delivery systems that, in order to be able to achieve constant delivery of the active substance over the period during which such patches are usually worn (3 days), rely upon amino-resistant silicone adhesives as the base polymer in which the scopolamine is present in both crystalline and solubilized form, and also include a rate controlling membrane.

A major disadvantage with systems as described above is that they are still susceptible to drug instability. Under appropriate conditions, the active agent may remain in crystalline form given its poor solubility in the base polymer, or may recrystallize or degrade in the presence of functional groups, vinyl acetate, or polar inactive substances in the formulations. Moreover, such systems require rate controlling membranes to achieve the appropriate drug delivery profile needed to effect therapy over the intended duration of use, adding to the cost and manufacturing burden. Membranes based on their desired copolymers with vinyl acetate may also further promote drug instability.

Thus, there remains a need for an improved dermal composition of drug carrier polymers that maintains solubilized drug stability, exhibits good adhesive and wear properties, and achieves a controllable drug flux and delivery profile for a suitable duration, such as three days, without the need for membranes, and that can be manufactured in commercially advantageous thicknesses and size.

SUMMARY

In accordance with one embodiment, there is provided a flexible, finite system for the transdermal administration of scopolamine, comprising: (a) a polymer matrix comprising a polymer blend consisting essentially of a blend of (i) a non-functional acrylic-based polymer constituting at least about 60% by weight of the dry weight of the polymer matrix, and (ii) an amine-resistant capped silicone polymer constituting not more than about 30% by weight of the dry weight of the polymer matrix; and (b) scopolamine solubilized in the polymer matrix, wherein the flexible, finite system is substantially free of vinyl acetate and polar components. In some embodiments, the scopolamine is scopolamine base.

In specific embodiments, the non-functional acrylic-based polymer is selected from the group consisting of non-functional polyacrylates, polyacrylics, and acrylate and acrylic polymers, such as non-functional homopolymers, copolymers and terpolymers of monomers selected from the group consisting of methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate, methacrylate, N-butyl acrylate, butyl methacrylate, ethyl methacrylate, methyl methacrylate, hexyl methacrylate, and methyl acrylate, and corresponding methacrylic acid esters and acrylic acid esters. In one specific embodiment, the non-functional acrylic-based polymer is a polymer of methyl acrylate and 2-ethylhexyl acrylate monomers.

In specific embodiments, the amine-resistant capped silicone polymer has a silanol content of about 13,000 or less, per polymer, including a silanol content of about 7,700 or less, per polymer.

In some embodiments, the polymer matrix is a pressure-sensitive adhesive composition.

In accordance with some embodiments, there is a provided a flexible finite system as described above, wherein the polymer matrix further comprises a non-polar penetration enhancer that is substantially free of glycols, including a penetration enhancer that is a non-polar functional derivative of a fatty acid, a non-polar fatty acid or fatty alcohol, or that is oleyl alcohol.

In accordance with some embodiments, the polymer matrix comprises an amount of non-polar penetration enhancer selected from the group consisting of less than about 10% by weight, less than about 5% by weight, and less than about 3% by weight, based on the dry weight of the polymer matrix.

In accordance with some embodiments, the polymer matrix comprises an amount of drug solubilized therein selected from the group consisting of from about 0.1% to about 30%, from about 0.3% to about 30%, from about 0.5% to about 15%, from about 1% to about 10%, and less than about 5%, by weight, based on the dry weight of the polymer matrix.

In accordance with specific embodiments, there is provided a flexible, finite system as described above, wherein the polymer matrix comprises not more than about 85% by weight of the non-functional acrylic-based polymer, not more than about 30% by weight of the amine-resistant capped silicone polymer, and about 10% or less by weight of a penetration enhancer, based on the total dry weight of the polymer matrix. In specific embodiments, the polymer matrix further comprises an amount of drug solubilized therein of from about 1% to about 10% by weight, based on the dry weight of the polymer matrix.

In accordance with specific embodiments, there is provided a flexible, finite system as described above, wherein the polymer matrix comprises (i) an amount of non-functional acrylic-based polymer of about 76% by weight, based on the dry weight of the polymer matrix, (ii) an amount of amine-resistant capped silicone polymer of about 12% by weight, based on the dry weight of the polymer matrix, (iii) an amount of scopolamine base solubilized therein of about 6% by weight, based on the dry weight of the polymer matrix, and (iv) an amount of oleyl alcohol of about 6%, by weight, based on the dry weight of the polymer matrix.

In accordance with specific embodiments, there is provided a flexible, finite system as described above, wherein the wt/wt ratio of non-functional acrylic-based polymer to amine-resistant capped silicone polymer in the polymer matrix is selected from the group consisting of at least about 3:1, at least about 3.5:1, at least about 4:1, at least about 4.5:1, at least about 5:1, at least about 5.5:1 and at least about 6:1.

In some embodiments, the flexible, finite system does not comprise a rate controlling membrane. In some embodiments, the flexible, finite system further comprises a backing layer and/or a release liner.

In accordance with another embodiment, there is provided a method of making a flexible, finite system as described above, comprising: (A) mixing in a volatile solvent amounts of (i) the non-functional acrylic-based polymer, (ii) the amine-resistant capped silicone polymer, and (iii) scopolamine, (B) casting the mixture; and (C) removing the volatile solvent to yield a dry polymer matrix, wherein the amounts of components (i), (ii) and (iii) used are selected to result in a polymer matrix comprising at least 60% by weight of the non-functional acrylic-based polymer and not more than 30% by weight of the amine-resistant capped silicone polymer, based on the dry weight of the polymer matrix.

In some embodiments of the method described above, step (A) comprises mixing in a volatile solvent (i) the non-functional acrylic-based polymer, (ii) the amine-resistant capped silicone polymer, (iii) the scopolamine and (iv) a non-polar penetration enhancer that is substantially free of glycols, wherein the amounts of components (i), (ii), (iii) and (iv) used are selected to result in a polymer matrix comprising at least 60% by weight of the non-functional acrylic-based polymer and not more than 30% by weight of the amine-resistant capped silicone polymer, based on the dry weight of the polymer matrix.

In accordance with another embodiment, there is provided a method of effecting transdermal scopolamine delivery comprising applying the flexible finite system as described above to the skin of a subject in need thereof.

BRIEF DESCRIPTION OF THE DRAWING

FIG. 1 is a graphical representation of average scopolamine flux through cadaver skin from an in-vitro permeation study over 72 hours comparing a transdermal adhesive system comprising a dermal composition of the present invention with the commercially available product Transderm Scop®.

DETAILED DESCRIPTION

As used herein, the singular forms "a," "an," and "the" designate both the singular and the plural, unless expressly stated to designate the singular only.

The term "about", and the use of ranges in general whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described composition (e.g., flexible, finite system, polymer matrix, etc.) comprises less than about 5%, less than about 3%, or less than about 1% by weight, based on the total weight of the composition at issue, of the excluded component.

As used herein "patient" denotes any animal in need of drug therapy, including humans.

As used herein, the phrases "therapeutically effective amount" and "therapeutic level" mean that drug dosage or plasma concentration in a subject that provides the specific pharmacological response for which the drug is administered in a patient in need of such treatment. It is emphasized that a therapeutically effective amount or therapeutic level of a drug that is administered to a particular patient in a particular instance will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human patients. Those skilled in the art can adjust such amounts in accordance with standard practices.

As used herein, the term "dermal" refers to delivery, administration or application of a drug by means of direct contact with tissue, such as skin or mucosa. Such delivery, administration or application is also known as percutaneous, transdermal, transmucosal and buccal. Similarly, "skin" is meant to include mucosa which further includes oral, buccal, nasal, rectal and vaginal mucosa.

As used herein, a "dermal composition" is defined as a composition which contains one or more drugs solubilized therein. The dermal composition is applied to a dermal area, as described above, for dermal administration or topical application of the one more drugs. A dermal composition may comprise a polymer matrix with the one or more drugs contained therein. As described below, in one embodiment, the polymer matrix is a pressure-sensitive adhesive for direct attachment to a user's (e.g., a patient's) skin. Alternatively, the polymer matrix may be non-adhesive and may be provided with separate adhesion means (such as a separate adhesive layer) for adhering the composition to the user's skin.

As used herein, the term "solubilized" is intended to mean that in the dermal composition there is an intimate dispersion or dissolution of the active agent (e.g., drug) at the crystalline, molecular or ionic level. As such, the solublized active agent is considered herein to be in "non-crystallized" form when in the compositions of the present invention.

As used herein, "matrix" is defined as a polymer composition which incorporates a therapeutically effective amount of the drug therein. The matrix may be monolithic and comprise a pressure-sensitive adhesive, or it may use separate attachment means for adhering or holding to the user's skin, such as a separate adhesive layer. A dermal drug delivery system comprising a matrix may optionally include additional drug supply means for continuously replenishing the drug supply in the matrix.

As used herein "monolithic" is defined as a device comprising a matrix composition which is adhesive, e.g., pressure-sensitive adhesive, bioadhesive, or otherwise.

As used herein, a polymer is an "adhesive" if it has the properties of an adhesive per se, or if it functions as an adhesive by the addition of tackifiers, plasticizers, crosslinking agents or other additives.

In accordance with one embodiment, there is provided an improved dermal composition comprising a polymer matrix with solubilized drug that can maintain solubilized drug stability, exhibits good adhesive and wear properties, and achieves a controllable drug flux and delivery profile for a duration of three days without the need for membranes, and that can be manufactured in commercially advantageous thicknesses and size, including sizes of 2.5 $cm^2$ and smaller.

In accordance with one embodiment, there is provided compositions and methods for delivering amino-functional drugs and drugs which, in a liquid state at ambient temperatures, form a crystalline hydrate upon exposure to water, or that are otherwise adversely affected in the presence of functional groups, vinyl acetate and/or strongly polar or acidic inactive substances. In one specific embodiment the drug is scopolamine, including scopolamine base. The compositions described herein may reliably reduce or inhibit recrystallization and degradation of the active agent and achieve controlled and constant drug release rates over a pre-determined application duration, such as for 3 days or more.

The term "amino-functional" is intended to mean a drug or active agent that may comprise one or more primary amine radicals, such as phenylpropanolamine, secondary amine radicals such as propranolol, or tertiary amine radicals such as theophylline and chlorpheniramine. The term also includes heterocyclic amine radicals such as those found in theophylline and diethylcarbomazine, and salts of amine-functional drugs, provided that they can be delivered transdermally. As used herein, the term does not include oxidized nitrogen radicals such as nitro radicals. Examples of amine-functional drugs for transdermal drug delivery include, for example, scopolamine, tetracaine, ephedrine, clonidine, nicotine, ramipril, enalapril, fentanyl and analogs such as alfentanyl, carfentanyl, lofentanyl, remifentanyl, sufentanyl, and trefentanyl, amphetamine, dextroamphetamine, methamphetamine, and atropine. Further examples of amino-functional drugs for use in transdermal drug delivery systems will be apparent to those skilled in the art.

Although, for the sake of convenience, the compositions and methods are described and illustrated hereafter with respect to a dermal composition for scopolamine delivery, the invention is not so limited, but includes compositions for delivery of amino-functional drugs and drugs which, in a liquid state at ambient temperatures, forms a crystalline hydrate upon exposure to water, as has been described in the prior art. Such drugs as nicotine, secoverine and benztropine, and any others described above or known in the art, may advantageously be formulated in the compositions described therein. In some embodiments, the drug, to the extent it exhibits a tendency to form crystalline hydrates, is stabilized in the described compositions.

In one embodiment, the transdermal systems contemplated for practicing the methods and compositions described here are in the form of a flexible, finite system. The phrase "flexible, finite system" is intended to mean a substantially non-aqueous, solid form, capable of conforming to the surface with which it comes into contact, and which is capable of maintaining the contact in such solid form so as to facilitate topical application without adverse physiological response, and without being appreciably decomposed by aqueous contact during topical application to a patient. Many such devices are known in the art and commercially available, such as transdermal drug delivery patches. Examples of suitable flexible, finite systems include those in which the drug is solubilized directly in an adhesive matrix, such as a pressure-sensitive adhesive, that also serves as the means for attaching the system to the skin or mucosa of a patient.

The flexible finite systems also may include a drug impermeable backing layer or film on one side of the adhesive layer, and a release liner on the other side. When present, the backing layer protects the adhesive layer of the flexible finite system or transdermal patch from the environment and prevents loss of the drug and/or release of other adhesive layer components to the environment. When present, the release liner is removed from the system to expose the adhesive layer prior to topical application. Materials suitable for use as release liners and backing layers are well-known known in the art.

Amino functional drugs, such as scopolamine, and in particular scopolamine base, can be unstable and undergo degradation (loss of bioavailable active drug) or undesirable changes (such as drug recrystallization, color changes or disadvantageous drug delivery onset and duration) in the presence of functional groups and vinyl acetate which are often present in dermal compositions, such as adhesives, enhancers, excipients and other carrier components, and more strongly polar or acidic inactive substances, such as glycols, that are typically present in dermal compositions. A major degradant/metabolite of scopolamine appears to be tropic acid, which can be present at a fifteen-fold increase in dermal compositions that include such groups or components, as compared to its level in dermal composition that are substantially free of such groups or components. Such degradation can greatly reduce the amount of the active drug during storage of the composition, thus reducing the amount of active drug available for drug delivery over the intended duration of treatment.

Further instability, in the form of recrystallization of the drug in the presence of moisture, or a yellowing or darkening color change which is undesirable in a finished product, may also occur in the presence of vinyl acetate or strongly polar or acidic substances typically used to increase solubility or permeation, such as glycols, including diproplyene glycol. Thus, while fatty acids, fatty alcohols, glycols, vinyl acetate and adhesives containing vinyl acetate monomer units, such as ethylene/vinyl acetate copolymers, and vinyl pyrrolidone/vinylacetates, have been found to work satisfactorily in transdermal compositions, their use may have some disadvantages.

In addressing the foregoing, the flexible, finite systems and compositions described herein provide dermal drug delivery systems comprising a polymer matrix having good adhesion properties and controllable drug solubility and flux that avoids instability from recrystallization, degradation or color change of the active substance.

In one embodiment, the flexible, finite systems and compositions described herein are substantially free of vinyl acetate, substantially free of polar components, or substantially free of both vinyl acetate and polar components. By "substantially free" is meant that the flexible, finite systems and compositions are free from amounts of vinyl acetate and/or polar components that negatively impact stability, e.g., that contribute to degradation, recrystallization, or other undesirable changes, in the drug or composition. For example, in some embodiments, the flexible, finite systems and compositions comprise less than about 5%, less than about 3%, or less than about 1% by weight, based on the total dry weight of the flexible, finite systems and compositions, of vinyl acetate and/or polar components. Thus, the flexible, finite systems and compositions may comprise less than 5%, less than 3%, or less than 1% by weight, based on the total dry weight of the flexible, finite systems and compositions, of vinyl acetate and/or polar components, or may comprise no vinyl acetate and/or polar components.

In some embodiments, the polymer matrix comprises a blend of two or more polymers. As used herein, the terms "blend" and "mixture" mean that there is no, or substantially no, chemical reaction or crosslinking (other than simple H-bonding) between the different polymers in the matrix or polymer carrier. However, crosslinking within a single polymer component is fully contemplated to be within the scope of the blends described herein.

In one embodiment, the polymer matrix comprises an acrylic-based polymer having good solubility for the drug but no or substantially no functional or reactive groups, blended with a second polymer, such as an amine compatible or capped silicone-based polymer, such that the matrix has sufficient wear properties, and is substantially free of weak organic acids or acidic inactive or auxiliary ingredients or excipients.

As used herein, "acrylic-based" polymer is defined as any polyacrylate, polyacrylic, acrylate or acrylic polymer. The acrylic-based polymers can be any of the homopolymers, copoly-mers, terpolymers, and the like of various acrylic acids or esters. The acrylic-based polymers useful in the compositions described herein include polymers of one or more monomers of acrylic acids and other copolymerizable monomers. The acrylic-based polymers also include copolymers of alkyl acrylates and/or methacrylates and/or copolymerizable secondary monomers. In some embodiments, the acrylic-based polymers are adhesive polymers. In other embodiments, the acrylic-based polymers function as an adhesive by the addition of tackifiers, plasticizers, crosslinking agents or other additives.

As used herein "non-functional acrylic-based" polymer is defined as an acrylic-based polymer which has no or substantially no functional reactive moieties present in the acrylic, e.g., is substantially free of functional reactive moieties. These are generally acrylic esters which can be copolymerized with other monomers which do not have functional groups (such as vinyl acetate). Thus, in one embodiment, the non-functional acrylic-based polymer does not include any vinyl acetate moieties. As used herein, the phrase "substantially free of functional reactive moieties" means that the acrylic polymer is free from amounts of functional reactive moieties that negatively impact stability, e.g., that contribute to degradation, recrystallization, or other undesirable changes, in the drug or composition. Thus, in some embodiments, the non-functional acrylic-based polymer comprise less than about 5%, less than about 3%, or less than about 1% by weight, based on the total weight of the acrylic polymer, of functional reactive moieties. Thus, the non-functional acrylic-based polymer may comprise less than 5%, less than 3%, less than 1% by weight, based on the total weight of the acrylic polymer, of functional reactive moieties, or may comprise no functional reactive moieties.

As used herein, "functional monomers or groups," are monomer units typically in acrylic-based polymers which have reactive chemical groups which modify the acrylic-based polymers directly or which provide sites for further reactions. Examples of functional groups include carboxyl, epoxy, hydroxyl, sulfoxyl, and amino groups. Acrylic-based polymers having functional groups are copolymers or terpolymers which contain, in addition to the nonfunctional monomer units described above, further monomer units having free functional groups. The monomers can be monofunctional or polyfunctional. These functional groups include carboxyl groups, hydroxy groups, amino groups, amido groups, epoxy groups, etc. Typical carboxyl functional monomers include acrylic acid, methacrylic acid, itaconic acid, maleic acid, and crotonic acid. Typical hydroxy functional monomers include 2-hydroxyethyl methacrylate, 2-hydroxyethyl acrylate, hydroxymethyl acrylate, hydroxymethyl methacrylate, hydroxyethyl acrylate, hydroxyethyl methacrylate, hydroxypropyl acrylate, hydroxypropyl methacrylate, hydroxybutyl acrylate, hydroxybutyl methacrylate, hydroxyamyl acrylate, hydroxyamyl methacrylate, hydroxyhexyl acrylate, hydroxyhexyl methacrylate. As noted above, in some embodiments, the acrylic polymer does not include such functional groups.

Non-functional acrylic-based polymers can include any acrylic based polymer having no or substantially no free functional groups. Exemplary acrylic based polymers include homopolymers, copolymers and terpolymers. The monomers used to produce the polymers can include alkyl acrylic, acrylic acid or methacrylic esters such as methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate, methacrylate, N-butyl acrylate, butyl methacrylate, ethyl methacrylate, methyl methacrylate, hexyl methacrylate, and methyl acrylate, and the corresponding methacrylic acid esters.

Further details and examples of acrylic-based polymers, including acrylic-based adhesives, functional monomers, and polymers which have no functional groups and which are suitable for use in the polymer matrices and compositions and methods described herein are known in the art and described, for example, in Satas, "Acrylic Adhesives," *Handbook of Pressure-Sensitive Adhesive Technology,* 2nd ed., pp. 396-456 (D. Satas, ed.), Van Nostrand Reinhold, N.Y. (1989); "Acrylic and Methacrylic Ester Polymers," *Polymer Science and Engineering*, Vol. 1, 2nd ed., pp 234-268, John Wiley & Sons, (1984); U.S. Pat. No. 4,390,520; and U.S. Pat. No. 4,994,267, all of which are expressly incorporated by reference in their entireties.

Exemplary suitable non-functional acrylic-based polymer adhesives which are commercially available include those sold under the trademark DURO-TAK® by National Starch and Chemical Corporation, Bridgewater, N.J.; HRJ 4483, 10127, and 11588 (non-functional acrylic-based pressure-sensitive adhesives) sold by Schenectady International, Inc., Schenectady, N.Y.; and Gelva-Multipolymer Acrylic Solutions sold by UCB Surface Specialties, Smyrna, Ga. (now Cytec Surface Specialties, Inc.). In one embodiment, the non-functional acrylic-based polymer is a polymer of methyl acrylate and 2-ethylhexyl acrylate monomers.

Typically, dermal drug delivery compositions made with high proportions of non-functional acrylic-based polymers do not have sufficient wear properties (e.g., adhesivity and cohesivity) for optimal performance. Thus, in some embodiments, there is an upper limit on the amount of non-functional acrylic-based polymer (including non-functional acrylic-based adhesive polymers) incorporated into the polymer matrix, such as an upper limit of 85% by weight, based on the total dry weight of the polymer matrix. This upper limit may vary with the drug being loaded into the composition, the drug loading amounts, the presence of other additives such as enhancers, and the type of the other polymer or adhesive, such as another acrylic-based polymer, used. Thus, for example, in some embodiments, the amount of non-functional acrylic-based polymer incorporated into the polymer matrix is up to about 85% by weight (e.g., about 85% or less), including at least about 60% by weight, at least about 65% by weight, at least about 70% by weight, at least about 75% by weight, or at least about 80% by weight, based on the total dry weight of the polymer matrix composition. Thus, in some embodiments, the non-functional acrylic-based polymer constitutes at least 60% by weight, at least 65% by weight, at least 70% by weight, at least 75% by weight, or at least 80% by weight of the polymer matrix, based on the total dry weight of the polymer matrix composition.

To improve the wear properties of dermal drug delivery compositions made with polymer matrices having high proportions of non-functional acrylic-based polymers, a second polymer can be included in the polymer matrix. In one embodiment, a second polymer is a non-irritating and non-sensitizing rubber-based, silicone-based or hydrocarbon polymer. In some embodiments, the second polymer comprises not more than about 30% by weight of the polymer matrix, based on the total dry weight of the polymer matrix, including about 30% by weight, not more than about 25% by weight, not more than about 20% by weight, not more than about 15% by weight, or not more than about 10% by weight of the polymer matrix, based on the total dry weight of the polymer matrix composition. Thus, for example, in some embodiments, the amount of second polymer incorporated into the polymer matrix is 30% by weight, not more than 30% by weight, not more than 25% by weight, not more than 20% by weight, not more than 15% by weight, or not more than 10% by weight of the polymer matrix, based on the total dry weight of the polymer matrix composition, such 30% or less by weight, 25% or less by weight, 20% or less by weight, 15% or less by weight, or 10% or less by weight.

The term "silicone-based" polymer is used interchangeably with the terms siloxane, polysiloxane, and silicones as used herein and as known in the art. A suitable silicone-based polymer may also be a pressure-sensitive adhesive. Thus, in some embodiments, the silicone-based polymer is an adhesive polymer. In other embodiments, the silicone-based polymer functions as an adhesive by the addition of tackifiers, plasticizers, crosslinking agents or other additives.

In one embodiment, the polymer matrix comprises a silicone-based polymer that is a polysiloxane adhesive prepared by cross-linking an elastomer, such as a high molecular weight polydiorganosiloxane, with a resin, to produce a three-dimensional siloxane structure, via a condensation reaction in an appropriate organic solvent. The ratio of resin to elastomer can be an important factor that can be adjusted to modify the physical properties of polysiloxane adhesives, as known in the art. See, e.g., Sobieski, et al., "Silicone Pressure Sensitive Adhesives," *Handbook of Pressure-Sensitive Adhesive Technology*, 2nd ed., pp. 508-517 (D. Satas, ed.), Van Nostrand Reinhold, N.Y. (1989). Further details and examples of silicone pressure-sensitive adhesives which are useful in the polymer matrices and compositions and methods described herein are mentioned in the following U.S. Pat. Nos. 4,591,622; 4,584,355; 4,585,836; and 4,655,767, which are all expressly incorporated by reference herein in their entireties. It should also be understood that silicone fluids are also contemplated for use in the polymer matrices and compositions and method described herein.

In some embodiments, polymer matrices comprising a silicone-based polymer as a second polymer are advantageous in dermal compositions containing amino-functional drugs, such as scopolamine. However, since amino-functional drugs can interact with silicone-based polymers by acting as catalysts for the condensation of silicone-bonded hydroxyl (silanol) groups (thereby resulting in loss of cohesivity and adhesivity) or be degraded/destabilized in the presence of such hydroxy groups, some embodiments use silicone-based polymers having a reduced silanol content. Examples of silicone-based polymers having a reduced or low silanol concentration include those with a silicone-bonded hydroxyl content of about 13,000 or less (including 13,000 or less), about 7,700 or less (including 7,700 or less), or below about 7,700 (including below 7,700), per polymer.

In some embodiments, the silicone-based polymers having a reduced silanol are amine-resistant or amine compatible. As used herein, the term "amine-resistant or amine compatible" is intended to mean a silicone polymer wherein the silicone-bonded hydroxyl groups (Si—OH) have been substantially reduced or eliminated, typically by substitution with a hydrocarbon radical such as a methyl group (Si—CH$_3$). Thus, in some embodiments, the polymer matrix comprises an amine-resistant capped silicone polymer, such as an amine-resistant capped silicone polymer with a reduced silanol content, such as a silanol content of about 13,000 or less, or about 7,700 or less, per polymer.

Exemplary silicone-based polymers are adhesives (e.g., capable of sticking to the site of topical application), including pressure-sensitive adhesives. Illustrative examples of silicone-based polymers having reduced silanol concentrations include amine compatible silicone-based adhesives (and capped polysiloxane adhesives) such as those described in U.S. Pat. No. Re. 35,474 and U.S. Pat. No. 6,337,086, which are incorporated herein by reference in their entireties, and which are commercially available from Dow Corning Corporation under their BIO-PSA 7-4100, -4200 and -4300 product series (Dow Corning Corporation, Medical Products, Midland, Mich., for polysiloxane pressure-sensitive adhesives in organic solutions).

Other amino-functionalized silicones that may be suitable for use in the polymer matrices, compositions and methods described herein include, for example, Amodimethicone available as SM2658 from Costec, Inc., Dow Corning® 929 and 939 from Dow Corning Corp. and L650, 652 and ADM 6057E from Wacker Silicones Corporation; Trimethylsilylamodimethicone available as SF1708-D1, SM2101 and SM2115-D2 from Costec, Inc. Dow Corning® Q2-7224 and Q2-8220 from Dow Corning Corp. and L653, 655, 656 and ADM 3047E from Wacker Silicones Corporation.

In one embodiment, the polymer matrix comprises a polymer blend consisting essentially of a blend of (i) a non-functional acrylic-based polymer and (ii) an amine-resistant capped silicone polymer. By "consisting essentially of" is meant that the polymer blend does not include any other components that would alter the basic characteristics of the polymer blend. For example, such a polymer blend would be substantially free of vinyl acetate, polar components (such as glycols), and polymers comprising functional reactive moieties. Such a polymer blend may, however, include tackifiers, plasticizers, crosslinking agents and/or other additives for imparting adhesive properties, particularly in embodiments where the non-functional acrylic-based polymer and/or amine-resistant capped silicone polymer is/are not adhesives. Such a polymer blend also may include a non-polar penetration enhancer, as discussed below. In one embodiment of a final product, the polymer matrix also comprises an amino functional drug, such as scopolamine (including scopolamine base), solubilized therein In one embodiment, the polymer matrix comprises a non-polar penetration enhancer. A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving the solubility and diffusibility of the drug within the polymer carrier and those which improve percutaneous absorption, for example, by changing the ability of the stratum corneum to retain moisture, softening the skin, improving the skin's permeability, acting as penetration assistants or hair-follicle openers or changing the state of the skin including the boundary layer.

In one embodiment, the penetration enhancer is a non-polar fatty acid or a non-polar functional derivative of a fatty acid, such as a fatty alcohol, and including isosteric modifications of fatty acids or non-acidic derivatives of the carboxylic functional group of a fatty acid or isosteric modifications thereof. In one embodiment, the functional derivative of a fatty acid is an unsaturated alkanoic acid in which the —COOH group is substituted with a functional derivative thereof, such as alcohols, polyols, amides and substituted derivatives thereof, including esters, ethers and N,N'-disubstituted amides. The term "fatty acid" means a fatty acid that has four to twenty-four carbon atoms, and includes but is not limited to those derived from animals and plants. Exemplary derivatives are those based on oleic acid such as oleyl alcohol. In some embodiments, the penetration enhancer is oleyl alcohol.

In some embodiments, the penetration enhancer is substantially free of polar components, such as glycols, including dipropylene glycol. By "substantially free" is meant that the penetration enhancer is free from amounts of polar components, such as glycols, that negatively impact stability, e.g., that contribute to degradation, recrystallization, or other undesirable changes, in the drug or composition. For example, in some embodiments, the penetration enhancer comprise less than about 5%, less than about 3%, or less than about 1% by weight, based on the total weight of the penetration enhancer, of polar components. Thus, the penetration enhancer may comprise less than 5%, less than 3%, or less than 1% by weight, based on the total weight of the penetration enhancer, of polar components, such as glycols, or may comprise no polar components, e.g., may comprise no glycols.

In some embodiments, a penetration enhancer is used in an amount up to about 20% by dry weight of the polymer matrix, including up to 20% by weight, up to about 10% by weight, including 10% by weight, or less than about 10% by weight, including less than 10% by weight, less than about 5% by weight, including less than 5% by weight, or less than about 3% by weight, including less than 3% by weight, based on the dry weight of the polymer matrix.

In one embodiment, the flexible, finite system comprises (a) a polymer matrix consisting essentially of a polymer blend consisting of a blend of (i) a non-functional acrylic-based polymer and (ii) an amine-resistant capped silicone polymer, and (iii) a non-polar penetration enhancer that is substantially free of glycols, and (b) an amino functional drug, such as scopolamine (including scopolamine base) solubilized in the polymer matrix. By "consisting essentially of" is meant that the polymer matrix does not include any other components that would alter the basic characteristics of the polymer matrix. For example, such a polymer matrix would be substantially free of vinyl acetate, polar components (such as glycols), and polymers comprising functional reactive moieties. Such a polymer blend may, however, include tackifiers, plasticizers, crosslinking agents and/or other additives for imparting adhesive properties, particularly in embodiments where the non-functional acrylic-based polymer and/or amine-resistant capped silicone polymer is/are not adhesives.

In one embodiment, the polymer matrix comprises a polymer blend that consists of a blend of (i) a non-functional acrylic-based polymer, (ii) an amine-resistant capped silicone polymer and a (iii) penetration enhancer. Such a matrix does not include tackifiers, plasticizers, crosslinking agents or other additives. In one embodiment of a final product, the polymer matrix also comprises an amino functional drug, such as scopolamine (including scopolamine base), solubilized therein The amount of drug to be incorporated in the dermal composition (e.g., in the polymer matrix) varies depending on the particular drug, the desired therapeutic effect, and the time span for which the system is to provide therapy. For most drugs, the passage of the drugs through the skin will be the rate-limiting step in delivery. A minimum amount of drug in the system is selected based on the amount of drug which passes through the skin in the time span for which the system is to provide therapy. In some embodiments, a flexible, finite system is used over a period of about 3 days, or longer. Thus, in one embodiment, the flexible, finite systems comprise an amount of drug sufficient to deliver therapeutic levels of drug over a period of from 1 day to 3 days or longer, including for 1 day, for 3 days, or for longer.

Generally, the amount of drug solubilized in the polymer matrix can vary from about 0.1% to about 30% by weight of the dry weight of the polymer matrix. However, the polymer matrices and compositions described herein are particularly useful for drugs which are generally used in relatively low concentrations, such as from about 0.3% to about 30% by weight of the dry weight of the polymer matrix, including from about 0.5% to about 15% of the dry weight of the polymer matrix, from about 1% to about 10%, or less than about 5% by weight of the dry weight of the polymer matrix. Thus, the invention includes flexible, finite systems comprising a polymer matrix with drug solubilized therein, wherein the amount of drug is from 0.1 to 30%, from 0.3 to 30%, from 0.5 to 15%, from 1 to 10%, or less than 5%, by weight of the dry weight of the polymer matrix.

In some embodiments, the flexible, finite system comprises a polymer matrix comprising an amount of drug, such as scopolamine base, solubilized therein of about 6%, including 6%, based on the dry weight of the polymer matrix.

In some embodiments, the flexible, finite system comprises a polymer matrix comprising an amount of amine-resistant capped silicone polymer of about 12%, including 12%, based on the dry weight of the polymer matrix.

In some embodiments, the flexible, finite system comprises a polymer matrix comprising an amount of non-functional acrylic-based polymer of about 76%, including 76%, based on the dry weight of the polymer matrix.

In some embodiments, the wt/wt ratio of the non-functional acrylic-based polymer to the amine-resistant capped silicone polymer is at least about 3:1, at least about 3.5:1, at least about 4:1, at least about 4.5:1, at least about 5:1, at least about 5.5:1 or at least about 6:1. Thus, in some embodiments, the wt/wt ratio of the non-functional acrylic-based polymer to the amine-resistant capped silicone polymer is at least 3:1, at least 3.5:1, at least 4:1, at least 4.5:1, at least 5:1, at least 5.5:1 or at least 6:1, including about 3:1, about 4:1, about 4.5:1, about 5:1, about 5.5:1 and about 6.1.

In some embodiments, the weight per unit area of the polymer matrix of the flexible, finite system is in the range of from about 1 mg/cm$^2$ to about 20 mg/cm$^2$, including in the range of from about 1.5 mg/cm$^2$ to about 15 mg/cm$^2$. Thus, in some embodiments, the weight per unit area of the polymer matrix of the flexible, finite system is from 1 mg/cm$^2$ to 20 mg/cm$^2$, or from 1.5 mg/cm$^2$ to 15 mg/cm$^2$.

In some embodiments, the drug delivery rate achieved by the flexible, finite system is in the range of from about 0.01 mg to about 100 mg of active agent per day, including in the range of from about 0.1 mg to about 50 mg per day. Thus, in some embodiments, the drug delivery rate achieved by the flexible, finite system is in the range of from 0.01 mg to 100 mg of active agent per day, including in the range of from 0.1 mg to 50 mg per day. In some embodiments, these rates are achieved over a duration of application of at least about 3 days, such as at least 3 days, including 3 days.

In some embodiments, the drug delivery achieved by the flexible, finite system is bioequivalent to that achieved by a comparably sized Transderm Scop® product, as illustrated in FIG. 1. In some embodiments, this bioequivalent drug delivery is achieved over a duration of application of at least about 3 days, such as at least 3 days, including 3 days.

The polymer matrices of the present invention may also include a volatile processing solvent or "co-solvent" for the drug and/or polymer(s). In some embodiments, the solvent is a non-toxic, pharmaceutically acceptable substance, such as a liquid (but not including water), which does not substantially negatively affect the adhesion properties of the polymer matrix or flexible, finite system or the stability of the drug, and in which the drugs in the amounts employed are fully soluble. Suitable solvents include volatile liquids such as alcohols (e.g., methyl, ethyl, isopropyl alcohols and methylene chloride); ketones (e.g., acetone); aromatic hydrocarbons such as benzene derivatives (e.g., xylenes and toluenes); lower molecular weight alkanes and cycloalkanes (e.g., hexanes, heptanes and cyclohexanes); and alkanoic acid esters (e.g., ethyl acetate, n-propyl acetate, isobutyl acetate, n-butyl acetate, isobutyl isobutyrate, hexyl acetate, 2-ethylhexyl acetate or butyl acetate); and combinations and mixtures thereof.

In one embodiment, a transdermal drug delivery system is prepared by preparing a polymer matrix by (A) mixing (i) a non-functional acrylic-based polymer, (ii) an amine-resistant capped silicone polymer; and (iii) the drug (e.g., scopolamine, including scopolamine base), in a volatile solvent, (B) casting the mixture and (C) removing the volatile solvent to yield a dry polymer matrix. In some embodiments, the amounts of components used are selected to result in a polymer matrix comprising at least 60% by weight non-functional acrylic-based polymer and not more than 30% by weight amine-resistant capped silicone polymer, based on the dry weight of the polymer matrix. In one specific embodiment, a transdermal drug delivery system is prepared by preparing a polymer matrix by (A) mixing (i) a non-functional polyacrylate, (ii) an amine-resistant capped silicone polymer, (iii) a drug (e.g., scopolamine, including scopolamine base), and (iv) an enhancer that is substantially free of glycols in appropriate amounts in an appropriate volatile solvent (including co-solvents), (B) casting the mixture and (C) removing the solvent by evaporation to form a film to yield a dry polymer matrix. In some embodiments, the amounts of components used are selected to result in a polymer matrix comprising at least 60% by weight non-functional acrylic-based polymer and not more than 30% by weight amine-resistant capped silicone polymer, based on the dry weight of the polymer matrix. In some embodiments, the final polymer matrix or composition is substantially free of the volatile solvent, e.g. is substantially free solvents such as alkanols. Additionally, in some embodiments, the polymer matrix or composition is made without using water; thus, the final polymer matrix or composition is substantially free of water. Moreover, as discussed above, the final polymer matrix or composition may be substantially free of vinyl acetate and polar components (including glycols).

In some embodiments, the flexible, finite system comprises a polymer matrix with drug solubilized therein (e.g., an active substance-containing pressure-sensitive adhesive polymer matrix or monolithic body) having a defined geometric shape and further comprising a protective release liner (which is removed prior to use) disposed on one side of the matrix and a backing layer that is substantially impermeable to the drug and other components of the polymer matrix (including inactive ingredients) disposed on the other side of the matrix. In use, removal of the release liner exposes the polymer matrix (adhesive composition) which functions as both the drug carrier matrix and as the means of applying (e.g., adhering) the dermal system to the user. As noted above, in some embodiments, the flexible, finite systems described herein do not comprise a rate controlling membrane.

The flexible, finite system may be of any shape or size suitable for transdermal application. In one embodiment, the flexible, finite system has a surface area of about 2.5 cm$^2$.

As noted above, in embodiments where the polymer matrix comprises a pressure-sensitive adhesive, the polymer matrix can be used as an adhesive portion of any transdermal drug delivery system (e.g., a reservoir device), and can be used as one or more layers of a multi-layer system. Alternatively, a polymer matrix comprising a pressure-sensitive adhesive can comprise an adhesive monolithic device. In embodiments where the polymer matrix does not comprise an adhesive, but instead, for example, comprises a polymeric drug reservoir, those skilled in the art will understand the applicability of the same principles discussed above with respect to the selection of components to preserve drug stability.

In some embodiments, there is provided a method of effecting transdermal drug delivery by applying a flexible finite system as described herein to the skin of a subject in need thereof. In some embodiments, the flexible finite system comprises scopolamine, such as scopolamine base, and the flexible finite system is applied over a period of at least about 3 days, such as at least 3 days, including 3 days. In some embodiments, the method is effective to achieve therapeutic levels of scopolamine in the subject during the application period, such as for a period of at least about 3 days, such as at least 3 days, including 3 days.

EXAMPLE

The following specific example is included as illustrative of the dermal systems and polymer matrices and compositions described herein. This example is in no way intended to be limiting of the scope of the invention. Other aspects of the invention will be apparent to those skilled in the art to which the invention pertains.

As used herein, the term, "flux" is defined as the absorption of the drug through the skin or mucosa, and is described by Fick's first law of diffusion:

$$J = -D(dCm/dx),$$

where J is the flux in g/cm²/sec, D is the diffusion coefficient of the drug through the skin or mucosa in cm²/sec and Dcm/dx is the concentration gradient of the drug across the skin or mucosa.

The dermal composition used in this example was prepared by thoroughly mixing, on a % w/w wet basis:
8% of an amino-compatible polysiloxane adhesive (methylated trimethylated silica having 60% solids in ethyl acetate; Dow Corning Corporation, Medical Products, Midland, Mich.),
81.1% of a non-functional, non-crosslinked acrylate copolymer adhesive (38% solids in ethyl acetate; National Starch and Chemical Corporation, Bridgewater, N.J.),
2.4% of oleyl alcohol,
2.4% of scopolamine base and
6.1% ethyl acetate in a container.

The blend was cast on a polyester release liner (Scotch Pak® 1022; 3M: Minneapolis, Mich.) with a 15 mil wet gap applicator. The cast down was dried for five minutes at ambient temperature under a hood and for an additional five minutes in a convection air oven at 85° C. to drive-off the volatile processing solvents. Upon completion of this step, the release liner coated with the dried adhesive-drug composition was laminated to the polyester side of a polyester/ethylene vinyl acetate backing material (Scotch Pak® 9732). This yielded a composition having the following composition on a dry basis (i.e., after removal of the volatile solvents):

| COMPONENT | PERCENT BY WEIGHT |
|---|---|
| Polysiloxane Adhesive | 12 |
| Polyacrylate Adhesive | 76 |
| Oleyl Alcohol | 6 |
| Scopolamine Base | 6 |
| | 100 |

Flux studies of the matrix system were run against the commercially available product Transderm Scop®, using human cadaver skin conducted with stratum corneum obtained from split thickness cryopreserved cadaver skin by the heat separation technique (Kligman & Christopher, 88 Arch. Dermatol. 702 (1963)).

Three samples of the test compositions and control were cut into 0.5 cm² circular pieces, the release liners were removed, and the compositions were placed upon the stratum corneum. The skin-matrix samples were then mounted between the donor and receiver compartments on modified Franz cells, the skin side facing the receiver compartment containing a receiving solution of 7.5 ml of 0.9% NaCl and 0.01% NaN₃ magnetically stirred at about 300 rpm. The Franz cells were then placed in an incubator to maintain the samples at 32° C. At predetermined sampling intervals, the entire contents of the receiver compartment were collected for drug assaying, and the receiver compartments refilled with fresh receiving solutions. The permeation samples were then analyzed by HPLC.

The results of the in-vitro flux experiment using matrix systems according to the present invention are shown in FIG. 1 and demonstrate that flexible, finite systems for transdermal delivery of scopolamine based on adhesive polymer matrices described herein are bioequivalent to the commercial transdermal scopolamine product, and that the flexible, finite systems described herein achieve such results without the need for a rate controlling membrane while having improved stability.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

What is claimed is:

1. A flexible, finite system for the transdermal administration of scopolamine, comprising:
   (a) a polymer matrix comprising a polymer blend consisting essentially of a blend of (i) a non-functional acrylic-based polymer constituting at least about 60% by weight of the dry weight of the polymer matrix, and (ii) an amine-resistant capped silicone polymer constituting not more than about 30% by weight of the dry weight of the polymer matrix; and
   (b) scopolamine solubilized in the polymer matrix,
   wherein said flexible, finite system comprises less than 1% by weight of vinyl acetate and glycols.

2. The flexible, finite system of claim 1, wherein the non-functional acrylic-based polymer is selected from the group consisting of non-functional polyacrylates, polyacrylics, and acrylate and acrylic polymers.

3. The flexible, finite system of claim 2, wherein the non-functional acrylic-based polymer is selected from the group consisting of non-functional homopolymers, copolymers and terpolymers of monomers selected from the group consisting of methyl acrylate, ethyl acrylate, propyl acrylate, amyl acrylate, butyl acrylate, 2-ethylbutyl acrylate, hexyl acrylate, heptyl acrylate, octyl acrylate, nonyl acrylate, 2-ethylhexyl acrylate, decyl acrylate, dodecyl acrylate, tridecyl acrylate, methacrylate, N-butyl acrylate, butyl methacrylate, ethyl methacrylate, methyl methacrylate, hexyl methacrylate, and methyl acrylate, and corresponding methacrylic acid esters and acrylic acid esters.

4. The flexible, finite system of claim 1, wherein the non-functional acrylic-based polymer is a polymer of methyl acrylate and 2-ethylhexyl acrylate monomers.

5. The flexible, finite system of claim 1, wherein the amine-resistant capped silicone polymer has a silanol content of about 13,000 or less, per polymer.

6. The flexible, finite system of claim 5, wherein the amine-resistant capped silicone polymer has a silanol content of about 7,700 or less, per polymer.

7. The flexible, finite system of claim 1, wherein the polymer matrix is a pressure-sensitive adhesive composition.

8. The flexible, finite system of claim 1, wherein the polymer matrix further comprises a non-polar penetration enhancer.

9. The flexible, finite system of claim 8, wherein the penetration enhancer is a non-polar functional derivative of a fatty acid.

10. The flexible, finite system of claim 8, wherein the penetration enhancer is a non-polar fatty acid or fatty alcohol.

11. The flexible, finite system of claim 8, wherein the penetration enhancer is oleyl alcohol.

12. The flexible, finite system of claim 8, wherein the polymer matrix comprises an amount of non-polar penetration enhancer selected from the group consisting of less than about 10% by weight, less than about 5% by weight, and less than about 3% by weight, based on the dry weight of the polymer matrix.

13. The flexible, finite system of claim 1, wherein the scopolamine is scopolamine base.

14. The flexible, finite system of claim 1, wherein the polymer matrix comprises an amount of scopolamine solubilized therein selected from the group consisting of from about 0.1% to about 30%, from about 0.3% to about 30%, from about 0.5% to about 15%, from about 1% to about 10%, and less than about 5%, by weight, based on the dry weight of the polymer matrix.

15. The flexible, finite system of claim 1, wherein the polymer matrix comprises not more than about 85% by weight of the non-functional acrylic-based polymer, not more than about 30% by weight of the amine-resistant capped silicone polymer, and about 10% or less by weight of a penetration enhancer, based on the total dry weight of the polymer matrix.

16. The flexible, finite system of claim 15, wherein the polymer matrix further comprises an amount of scopolamine solubilized therein of from about 1% to about 10% by weight, based on the dry weight of the polymer matrix.

17. The flexible, finite system of claim 1, wherein the polymer matrix comprises (i) an amount of non-functional acrylic-based polymer of about 76% by weight, based on the dry weight of the polymer matrix, (ii) an amount of amine-resistant capped silicone polymer of about 12% by weight, based on the dry weight of the polymer matrix, (iii) an amount of scopolamine base solubilized therein of about 6% by weight, based on the dry weight of the polymer matrix, and (iv) an amount of oleyl alcohol of about 6%, by weight, based on the dry weight of the polymer matrix.

18. The flexible, finite system of claim 1, wherein the wt/wt ratio of non-functional acrylic-based polymer to amine-resistant capped silicone polymer in the polymer matrix is selected from the group consisting of at least about 3:1, at least about 3.5:1, at least about 4:1, at least about 4.5:1, at least about 5:1, at least about 5.5:1 and at least about 6:1.

19. The flexible, finite system of claim 1, wherein the flexible, finite system does not comprise a rate controlling membrane.

20. The flexible, finite system of claim 1, wherein the flexible, finite system further comprises a backing layer.

21. The flexible, finite system of claim 1, wherein the flexible, finite system further comprises a release liner.

22. A method of making a flexible, finite system of claim 1, comprising:
(A) mixing in a volatile solvent selected amounts of (i) the non-functional acrylic-based polymer, (ii) the amine-resistant capped silicone polymer, and (iii) scopolamine,
(B) casting the mixture; and
(C) removing the volatile solvent to yield a dry polymer matrix,
wherein the amounts of components (i), (ii) and (iii) are selected to result in a polymer matrix comprising at least 60% by weight of the non-functional acrylic-based polymer and not more than 30% by weight of the amine-resistant capped silicone polymer, based on the dry weight of the polymer matrix.

23. The method of claim 22, wherein, step (A) comprises mixing in a volatile solvent (i) the non-functional acrylic-based polymer, (ii) the amine-resistant capped silicone polymer, (iii) the scopolamine, and (iv) a non-polar penetration enhancer comprising less than 1% by weight glycols,
wherein the amounts of components (i), (ii), (iii) and (iv) used are selected to result in a polymer matrix comprising at least 60% by weight of the non-functional acrylic-based polymer and not more than 30% by weight of the amine-resistant capped silicone polymer, based on the dry weight of the polymer matrix.

24. A method of effecting transdermal scopolamine delivery comprising applying the flexible finite system of claim 1 to the skin of a subject in need thereof.

* * * * *